(12) United States Patent
Miller

(10) Patent No.: US 6,884,898 B1
(45) Date of Patent: Apr. 26, 2005

(54) PROPYLENE OXIDE PROCESS

(75) Inventor: Jay F. Miller, Chester Springs, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 6 days.

(21) Appl. No.: 10/730,420

(22) Filed: Dec. 8, 2003

(51) Int. Cl.$^7$ ............................................. C07D 301/06
(52) U.S. Cl. ........................................ 549/524; 549/532
(58) Field of Search ................................. 549/532, 524

(56) References Cited

U.S. PATENT DOCUMENTS

| | | |
|---|---|---|
| 5,646,314 A | 7/1997 | Crocco et al. |
| 6,005,123 A | 12/1999 | Dessau et al. |
| 6,008,388 A | 12/1999 | Dessau et al. |
| 6,323,350 B1 * | 11/2001 | Lindner et al. ............. 549/532 |
| 6,441,204 B1 | 8/2002 | Grey |
| 6,498,259 B1 | 12/2002 | Grey et al. |
| 6,555,493 B2 | 4/2003 | Cooker et al. |

FOREIGN PATENT DOCUMENTS

| | | |
|---|---|---|
| DE | 19600709 | 1/1996 |
| DE | WO9602323 | 2/1996 |
| JP | 4-352771 | 5/1991 |
| JP | H8-269029 | 3/1995 |
| JP | H8-269030 | 3/1995 |
| WO | WO9725143 | 7/1997 |
| WO | WO9731711 | 9/1997 |
| WO | WO9747386 | 12/1997 |

* cited by examiner

*Primary Examiner*—Amelia A. Owens
(74) *Attorney, Agent, or Firm*—William C. Long

(57) ABSTRACT

Propylene oxide is formed by reaction of propylene with molecular oxygen in a high boiling solvent containing slurried solid catalyst, the light components are flashed and the remaining liquid containing slurried catalyst is recycled.

6 Claims, 1 Drawing Sheet

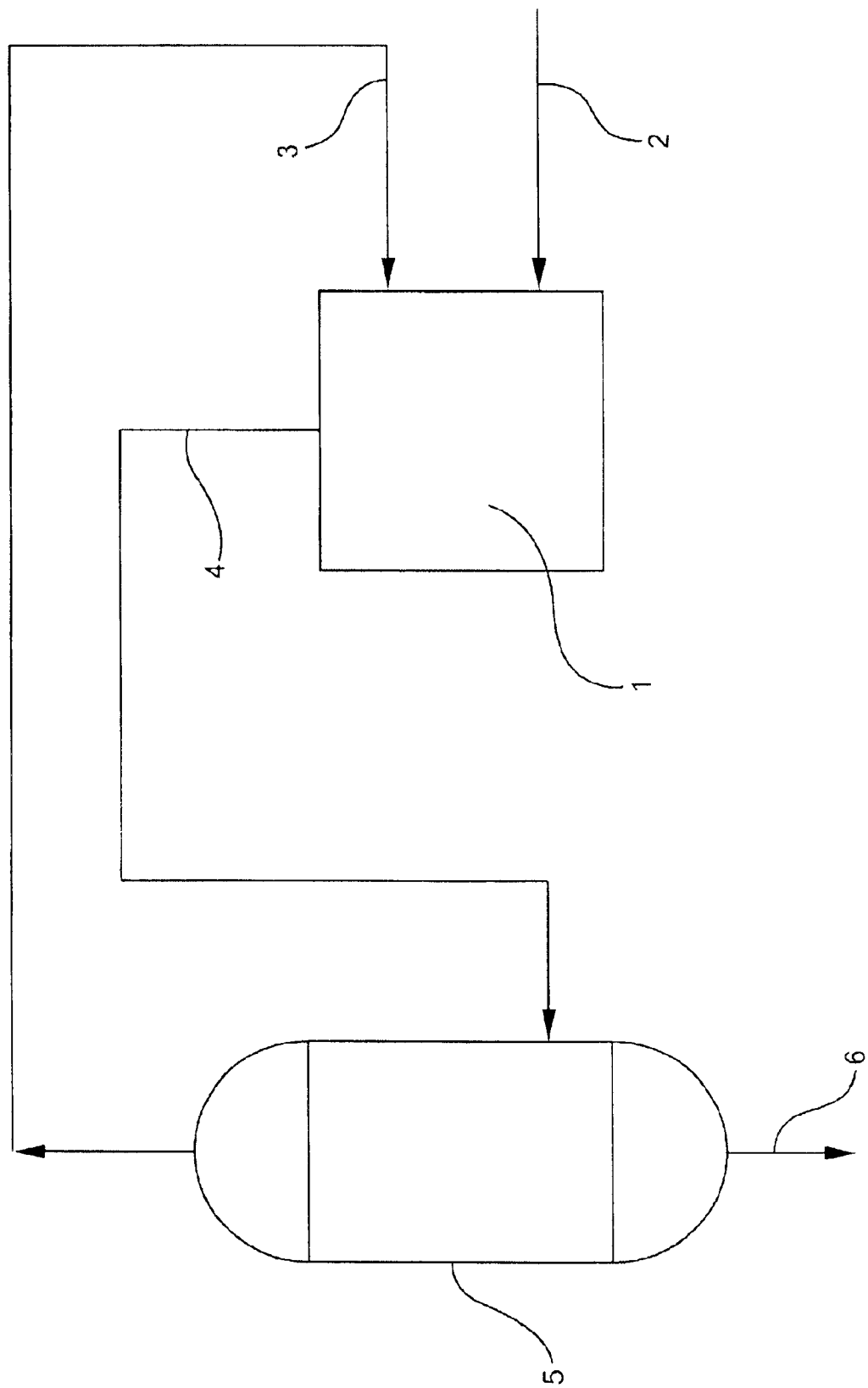

PROPYLENE OXIDE PROCESS

BACKGROUND OF THE INVENTION

1. Field of the Invention

The present invention relates to a process for the production of propylene oxide and especially to the work-up of propylene oxide production reaction mixtures.

2. Description of the Prior Art

Propylene oxide is produced commercially by the chlorohydrin process and by the Oxirane hydroperoxide process.

In an effort to improve the economics of propylene oxide production, a substantial amount of research has been done in an effort to develop a direct oxidation process to propylene oxide which does not involve the use of chlorine or the coproduction of another volume product such as styrene or methyl tertiary butyl ether.

Promising results have been achieved by oxidation procedures with molecular oxygen carried out in a liquid reaction mixture using as catalyst a slurry of solid catalyst particles in an appropriate solvent. See, for example, U.S. Pat. No. 6,441,204B1, U.S. Pat. No. 6,498,259B1, and U.S. Pat. No. 6,555,493B2, the disclosures of which are incorporated herein by reference.

SUMMARY OF THE INVENTION

In accordance with the present invention, a relatively high boiling solvent which may also contain methanol and/or water is used in the oxidation with solid catalyst slurried therein and the oxidation reaction mixture is continuously removed from the oxidation reactor with lighter materials including product propylene oxide being vaporized and recovered leaving the solid catalyst particles in the high boiling solvent liquid with this stream being recycled to the oxidation.

BRIEF DESCRIPTION OF THE DRAWING

The attached drawing illustrates schematically practice of the invention.

DETAILED DESCRIPTION

Referring to the drawing, reactor 1 is a conventional reactor for the oxidation of propylene to propylene oxide. Suitably, propylene, oxygen and hydrogen are introduced to reactor 1 via line 2. Although these components are illustrated as being introduced together, it will be understood that for reasons of safety and/or convenience the components can be introduced separately to reactor 1.

Also introduced to reactor 1 via line 3 is a slurry of solid epoxidation catalyst in a high boiling solvent and conditions are maintained in reactor 1 so as to insure thorough contact of the various materials at reaction conditions effective to form propylene oxide. Generally the catalyst particles slurried in the solvent range in size (diameter) from 5 to 100,000 nanometers.

Continuously removed from reactor 1 via line 4 is a stream of the reaction mixture which is comprised of the high boiling solvent, slurried catalyst particles, product propylene oxide, as well as unreacted feed components and various other materials which were fed to or formed in reactor 1. The reaction mixture is passed via line 4 to separator 5 which can be one or more of a flash separator or a distillation column.

An important feature of the invention is that in separator 5 the lighter materials are vaporized and removed via line 6 whereas the liquid high boiling solvent and slurried catalyst contained therein is separated via line 3 and recycled to reactor 1.

The use of the relatively non-volatile high boiling solvent permits the ready separation of low boiling components by vaporization from the reaction mixture whereby the non-vaporized solvent along with the contained catalyst particles can conveniently be recycled to the epoxidation reactor. The removed light components can, of course, be further treated as by distillation to recover propylene oxide product. Unreacted materials can, after separation, also be recycled where appropriate.

In certain processes, as exemplified in U.S. Pat. No. 6,008,388 and U.S. Pat. No. 6,005,123, improved oxirane compound production is achieved when various promoters or additives are incorporated in the reaction mixture. Examples are various phosphorous or nitrogen containing compounds as described in the above patents. Such additives may be relatively high boiling and in accordance with the present invention these additives can be retained in the high boiling solvent liquid phase with the slurried catalyst and returned to the reaction zone after separation of the light materials thus providing a special advantage of the present invention.

As will be appreciated, the process of the invention provides a convenient and improved procedure for the recovery of product propylene oxide when compared, for example, to the more conventional procedures which use lighter solvents such as methanol and/or water and which involve separation of catalyst particles for recycle by cumbersome filtration procedures. Such prior procedures have the additional disadvantage that the reactive propylene oxide product continues to react to form unwanted by-products such as propylene glycol and methoxy glycols during protracted separation procedures.

A key feature in practice of the present invention resides in the selection of a suitable high boiling solvent. The solvent should be stable and non-reactive at the conditions encountered in the process and have high solubility for hydrogen and oxygen as well as exhibiting high stability at the oxidation conditions.

The solvent should have a boiling point of at least 130° C., preferably at least 180° C. Examples of suitable solvents are silicone oils which may be water soluble or water insoluble, polyethylene glycol, polypropylene glycol, polyols, higher ethers such as tetraglyme, and the like. Especially preferred is methoxy propanol and dipropylene glycol monomethyl ether which are by-product of the reaction.

In general, the epoxidation reaction is carried out in accordance with known procedures. Preferred is the reaction of propylene, oxygen and hydrogen using a noble metal promoted titanium silicalite catalyst. Preferred titanium-containing zeolite catalysts suitable for use in the process of this invention will generally have a composition corresponding to the following empirical formula $xTiO_2$ $(1-x)SiO_2$ where x is between 0.0001 and 0.500. More preferably, the value of x is from 0.01 to 0.125. The molar ratio of Si:Ti in the lattice frame work of the zeolite is advantageously from 9.5:1 to 99:1 (most preferably from 9.5:1 to 60:1). The use of relatively titanium-rich zeolites may also be desirable. The zeolite may or may not contain extra framework titanium.

The catalyst preferably comprises a noble metal supported on the above described zeolites. While any of the noble metals can be utilized (i.e., gold, silver, platinum, palladium, iridium, ruthenium, osmium), either alone or in combination, palladium is particularly desirable. Typically, the amount of noble metal present in the catalyst will be in the range of from 0.01 to 5 weight percent, preferably 0.05 to 2 weight percent.

The titanium silcalite used is prepared by known procedures. A preferred feature is that the silicalite be subjected to an oxidative calcination as with air at elevated temperature, e.g. 300 to 850° C., illustratively 550° C., in accordance with known procedures prior to use in accordance with the invention. The calcination is carried out until substantially complete removal of organic residues is accomplished. Thorough pre-washing and oxidative calcination procedures are described, for example in JP H-269029 and JP H-269030.

The titanium silicalite washing and calcination is carried out so as to remove essentially all of the residues of materials such as templating agents and the like used in the silicalite preparation, especially ammonium-type materials.

The calcined silicalite essentially free of residues is then treated as by ion exchange or impregnation procedures in order to incorporate the desired noble metal into the silicalite in appropriate amounts. Of the procedures, ion exchange is preferred with subsequent essentially complete removal of anionic residues from the resulting catalyst. Impregnation procedures can be used as is described herein later.

Removal of essentially all residues from the noble metal containing support is important and is conventionally accomplished by water washing and filtering techniques. Multiple washing and filtering steps are especially preferred. Preferably the noble metal/titanium silicalite catalyst is then dried by gentle heating, for example under vacuum.

Preferably, the catalyst is subjected to an oxidative calcination at temperatures of at least 150° C. for illustratively 10 minutes to 24 hours. Calcination temperature in the range 150–650° C., preferably 250–600° C., and most preferably 300–550° C. are employed.

Additional improvements are also achieved where prior to or during epoxidation the catalyst is contacted with solutions buffered to slightly acid to basic pH. The preferred pH range is 5–8, preferably 6–7.5. See, for example, U.S. Pat. No. 5,646,314. Especially advantageous is the use of sodium, ammonium, and/or potassium salt buffered solutions. Excellent results are also achieved with calcium and magnesium salt containing solutions. Other Group I a and II a salts can be used as can compounds such as triphenyl phosphine. The combination of the calcination and contact with the buffered solution gives best results.

Especially preferred is the use of various promoters, most preferably phosphorous compounds as described in U.S. Pat. No. 6,005,123.

The process of propylene epoxidation may be suitably conducted under the reaction conditions (e.g., temperature, pressure, reactant ratios) described in the following published patent applications: WO 96/102323, WO 97/25143, DE 19600709, WO 97/31711, WO 97/47386, JP 4-352771, JP H8-269029, and H8-269030.

The amount of catalyst used may be determined on the basis of the molar ratio of the titanium contained in the titanium zeolite to the olefin that is supplied per unit of time. Typically, sufficient catalyst is present to provide a titanium/olefin fed ratio of from 0.00001 to 0.1 per hour. The time required for the epoxidation may be determined on the basis of the gas hourly space velocity, i.e., the total column of olefin, hydrogen, oxygen and carrier gas(es) per hour per unit of catalyst volume (abbreviated as GHSV). A GHSV in the range of 0.1 to 10,000 hr$^{-1}$ is typically satisfactory. The epoxidation is carried out in the liquid phase and it is advantageous to work at a pressure of 1–100 bars. Epoxidation according to the invention is carried out at a temperature effective to achieve the desired olefin epoxidation, preferably at temperatures in the range of 0–125° C. (more preferably, 20–80° C.). The molar ratio of hydrogen to oxygen can usually be varied in the range of $H_2:O_2$-1:10 to 5:1 and is especially favorable at 1:5 to 1:1. The molar ratio of oxygen to olefin can be 3:1 or more but preferably is 1:1 to 1:20, and most preferably 1:1.5 to 1:10. Relatively low $O_2$ to olefin molar ratios (e.g., 1:1 to 1:3) may be advantageous for certain olefins. As the carrier gas any desired inert gas can be used. The molar ratio of olefin to carrier gas is then usually in the range of 50:1 to 1:50, and especially 20:1 to 1:1.

As inert carrier gas, noble gases such as helium, neon, argon, krypton, and xenon are suitable in addition to nitrogen and carbon dioxide. Saturated hydrocarbons with 1–8, especially 1–6, and preferable with 1–4 carbon atoms, e.g., methane, ethane, propane, and n-butane, are also suitable. Nitrogen and saturated $C_1$–$C_4$ hydrocarbons are the preferred inert carrier gases. Mixtures of the listed inert carrier gases can also be used.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

In practice of the invention, a reaction mixture stream is continuously removed via line 4. In preferred practice, the stream is flashed in zone 5 at below atmospheric pressure up to about 50 psig preferably up to 10 psig, and at a temperature sufficient to vaporize the reaction mixture components which are lower boiling than the solvent. Illustrative vaporization temperatures are 100 to 150° C. The following example illustrates the invention.

EXAMPLE

Reactor 1 is a CSTR to which is fed via line 2 about 55 lbs/hr propylene, 20 lbs/hr oxygen and 0.7 lbs/hr hydrogen as well as 468 lbs/hr inerts.

Fed to reactor 1 via line 3 is a slurry of Pd on TS-1 comprising 0.1 wt % Pd prepared as described in U.S. Pat. No. 6,555,493B2 in dipropylene glycol monomethyl ether solvent. The solvent has a boiling point of about 188° C. and the solvent/catalyst slurry comprising 66 wt % catalyst is fed to reactor 1 at the rate of 105 lbs/hr. The slurried catalyst has an average particle size of about 30 microns.

In reactor 1 the reaction mixture is thoroughly agitated to ensure good contact between the various compounds. The reaction conditions in reactor 1 include a reaction temperature of 60° C. and a reaction pressure of about 33 bars. Residence time is about 240 minutes. A reaction mixture stream is removed via line 4 at the rate of about 649 lbs/hr, the composition by weight of this stream is about 16% solvent. 4% propylene oxide, 1% oxygen, 0.05% hydrogen, 1% propane, and 79% other lights, and the stream is passed to flash separator 5 wherein the stream is flashed at 150° C. and 2 bars. An overhead stream is removed via line 6 at a rate of about 544 lbs/hr. This stream comprises about 4.6 wt % propylene oxide and is passed to separation for recovery of propylene oxide.

Liquid bottoms comprising 9.5 wt % catalyst in the solvent is removed via line 3 and recycled to reactor 1 at the rate of 105 lbs/hr. Make-up solvent with slurried catalyst is added as needed to line 3 (not shown).

I claim:

1. In a continuous process for the production in a reaction zone of propylene oxide by reacting propylene with molecular oxygen and hydrogen at reactive conditions in a liquid solvent containing a solid noble metal on titanium silicalite epoxidation catalyst slurried in the solvent, the improvement which comprises employing a solvent having a boiling point of at least 130° C., continuously removing a reaction liquid stream from the reaction zone, flashing lower boiling components comprising propylene oxide as vapor from the said reaction liquid stream and recycling a liquid slurry of solvent and catalyst slurry from the flashing step to the oxidation reaction zone.

2. The process of claim 1 wherein the solvent has a boiling point of at least 180° C.

3. The process of claim 1 wherein the solvent is dipropylene glycol monomethyl ether.

4. The process of claim 1 wherein the solvent is methoxy propanol.

5. The process of claim 1 wherein the solid epoxidation catalyst comprises a noble metal on TS-1.

6. The process of claim 1 wherein the solid epoxidation catalyst comprises Pd on TS-1.

* * * * *